United States Patent
Guo et al.

(10) Patent No.: US 7,252,837 B2
(45) Date of Patent: *Aug. 7, 2007

(54) HEMOSTATIC WOUND DRESSING AND METHOD OF MAKING SAME

(75) Inventors: Jian Xin Guo, Bridgewater, NJ (US); Dwayne Lee Looney, Flemington, NJ (US); Guanghui Zhang, Belle Mead, NJ (US); Anne Jessica Gorman, Hightstown, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/186,021

(22) Filed: Jun. 28, 2002

(65) Prior Publication Data

US 2004/0001879 A1    Jan. 1, 2004

(51) Int. Cl.
*A61F 13/00* (2006.01)
*A61L 15/00* (2006.01)

(52) U.S. Cl. .................. 424/443; 424/445; 424/446; 424/447

(58) Field of Classification Search ............ 424/443, 424/484–489
See application file for complete search history.

(56) References Cited

U.S. PATENT DOCUMENTS

| | | |
|---|---|---|
| 2,517,772 A | 8/1950 | Doub et al. |
| 2,773,000 A | 12/1956 | Masci et al. |
| 2,914,444 A | 11/1959 | Smith |
| 3,328,259 A | 6/1967 | Anderson |
| 3,328,529 A | 6/1967 | Anderson |
| 3,364,200 A | 1/1968 | Aston et al. |
| 3,868,955 A | 3/1975 | Siragusa et al. |
| 4,289,824 A | 9/1981 | Smith |
| 4,407,787 A | 10/1983 | Stemberger |
| 4,600,574 A | 7/1986 | Lindner et al. |
| 4,626,253 A | 12/1986 | Broadnax, Jr. |
| 4,752,466 A | 6/1988 | Saferstein et al. |
| 4,840,626 A | 6/1989 | Linsky et al. |
| 5,134,229 A | 7/1992 | Saferstein et al. |
| 5,180,398 A | 1/1993 | Boardman et al. |
| 5,409,703 A | 4/1995 | McAnalley et al. |
| 5,643,596 A | 7/1997 | Pruss et al. |
| 5,645,849 A | 7/1997 | Pruss et al. |
| 5,821,343 A | 10/1998 | Keogh |
| 5,866,165 A | 2/1999 | Liu et al. |
| 5,914,118 A | 6/1999 | Yamamura et al. |
| 5,925,552 A | 7/1999 | Keogh et al. |
| 5,945,319 A | 8/1999 | Keogh |

(Continued)

FOREIGN PATENT DOCUMENTS

CS            217243 B      12/1982

(Continued)

OTHER PUBLICATIONS

European Search Report EP03254114 dated Dec. 17, 2003.

(Continued)

*Primary Examiner*—Isis Ghali (57) ABSTRACT

The present invention is directed to wound dressings that contain a fabric made from biocompatible polymeric fibers and having flexibility, strength and porosity effective for use as a hemostat, and a porous, polymeric matrix prepared from a biocompatible, water-soluble or water-swellable polymer dispersed through the fabric; and to methods of making such wound dressings.

9 Claims, 9 Drawing Sheets

U.S. PATENT DOCUMENTS

| | | |
|---|---|---|
| 6,017,741 A | 1/2000 | Keogh |
| 6,214,808 B1 | 4/2001 | Soe et al. |
| 6,261,679 B1 | 7/2001 | Chen et al. |
| 6,306,424 B1 | 10/2001 | Vyakarnam et al. |
| 6,333,029 B1 | 12/2001 | Vyakarnam et al. |
| 6,365,149 B2 | 4/2002 | Vyakarnam et al. |
| 6,500,777 B1 | 12/2002 | Wiseman et al. |
| 2001/0025154 A1 | 9/2001 | Rapp |
| 2002/0012693 A1 | 1/2002 | Cohen et al. |
| 2002/0120348 A1 | 8/2002 | Melican et al. |
| 2003/0073663 A1 | 4/2003 | Wiseman et al. |
| 2004/0005350 A1 | 1/2004 | Looney et al. |

FOREIGN PATENT DOCUMENTS

| | | |
|---|---|---|
| CS | 235108 B1 | 5/1985 |
| CS | 238016 B1 | 11/1985 |
| EP | 0 177 064 A | 4/1986 |
| EP | 0 216 378 A2 | 4/1987 |
| EP | 0 372 969 A | 6/1990 |
| EP | 0468114 A2 | 1/1992 |
| EP | 0 636 378 A | 2/1995 |
| EP | 0 815 879 A2 | 6/1997 |
| EP | 1172115 A1 | 1/2002 |
| EP | 1 378 255 A2 | 1/2004 |
| GB | 942 305 A | 11/1963 |
| GB | 983 073 A | 2/1965 |
| GB | 2 314 840 A | 8/1996 |
| GB | 2 314 842 A | 1/1998 |
| GB | 2 344 519 A | 6/2000 |
| IN | 159332 | 5/1987 |
| JP | 60-87225 A | 5/1985 |
| RU | 2146264 C1 | 3/2000 |
| WO | WO 96/016643 A | 6/1996 |
| WO | WO 96/040033 A1 | 12/1996 |
| WO | WO 98/00180 A1 | 1/1998 |
| WO | WO 98/000446 A | 1/1998 |
| WO | WO 98/033479 A | 8/1998 |
| WO | WO 99/01168 A1 | 1/1999 |
| WO | WO 01/23653 A1 | 4/2001 |
| WO | WO 02/02155 A1 | 1/2002 |
| WO | WO 01/22059 A1 | 3/2002 |
| WO | WO 02/022059 A1 | 3/2002 |
| WO | WO 02/058750 A2 | 8/2002 |
| WO | WO 03/020191 A | 3/2003 |

OTHER PUBLICATIONS

Hercules, Acqualon Division, "Aqualon® Sodium Carboxymethylcellulose—Product Specifications," Hercules Incorporated, 1997, pp. No. 4116-4.

Hercules, Acqualon Division, "Aqualon® Sodium Carboxymethylcellulose—Physical and Chemical Properties," Hercules Incorporated, 1995, pp. 1-27.

European Search Report dated Jul. 8, 2004, for corresponding EP application 03254091.6.

European Search Report dated Apr. 2, 2004, for corresponding EP application 03254119.5.

U.S. Appl. No. 10/304,781, Pendharkar et al.

U.S. Appl. No. 10/305,040, Pendharkar.

U.S. Appl. No. 10/304,472, Gorman et al.

U.S. Appl. No. 10/326,244, Zhang et al.

U.S. Appl. No. 10/396,224, Looney et al.

U.S. Appl. No. 10/448,878, Pendharkar

U.S. Appl. No. 10/603,320, Looney et al.

U.S. Appl. No. 10/721,836, Looney et al.

Arand et al., "Intraoperative Chemical Hemostasis in Neurosurgery", Neurosurgery, vol. 18, No. 2, pp. 223-233 (1986).

ASTM (American Society for Testing and Materials), Designation: E11-87, "Standard Specification for Wire-Cloth Sieves for Testing Purposes" pp. 13-16 (1987).

Davidson, "7-The Properties of the Oxycelluloses Formed in the Early Stages of the Oxidation of Cotton Cellulose by Periodic Acid and Metaperiodate", The Journal of the Textile Institute—Transactions, pp. T81-T96 (Jul. 1940).

Edwards et al., "Modified Cotton Gauze Dressing that Selectively Absorb Neutrophil Elastase Activity in Solution", Wound Repair and Regeneration, vol. 9, No. 1, pp. 50-58, The Wound Healing Society (2001).

Frantz et al., "Oxidized Cellulose-Absorbable Gauze (Cellulosic Acid)", Journal of American Medical Association, vol. 129, pp. 798-801 (Nov. 1945).

Frantz, "New Absorbable Hemostatic Agents", The Bulletin, vol. 22, pp. 102-110 (1946).

Jackson et al., "Application of the Cleavage Type of Oxidation by Periodic Acid to Starch and Cellulose", Journal of American Chemistry Society, vol. 59, pp. 2049-2050 (Oct. 1937).

Lucas, "Inactivation of Thrombin by Oxidized Cellulose", Journal of Oral Therapeutics and Phamacology, vol. 3, No. 4, pp. 262-268 (1967).

Matras, "Fibrin Seal: The State of the Art", Journal of Oral Maxillofac Surg., vol. 43, No. 8, pp. 605-611 (1985).

Singh et al., "An Insulin Delivery System from Oxidized Cellulose", Journal of Biomedical Materials Research, vol. 15, pp. 655-661 (1981).

Sinha et al., "Blood-Cellulosics Interactions", Biomat., Medical Devices, Artificial Organs, No. 12(3-4), pp. 273-287 (1984-1985).

Stilwell et al., "15. Oxidized Cellulose: Chemistry, Processing Medical Applications", Handbook of Biodegradable Polymers, Edited by Domb et al., pp. 291-306 (1997).

Turaev et al., "Hemostatic Activity and Reabsorbability of Carboxymethyl Cellulose", Khim.-Farm. Zh., 24(8), pp. 47-51 (1990) (English Abstract).

European Search Report dated Oct. 25, 2004, for corresponding EP application 04253808.2.

HEMOSTATIC WOUND DRESSING AND METHOD OF MAKING SAME

FIELD OF THE INVENTION

The present invention relates to hemostatic wound dressings, more specifically, a flexible hemostatic patch comprising a knitted fabric of oxidized cellulose and a porous water-soluble or water-swellable polymeric matrix, and to a process of making such fabrics and wound dressings.

BACKGROUND OF THE INVENTION

The control of bleeding is essential and critical in surgical procedures to minimize blood loss, postsurgical complication and to shorten the duration of the surgery in the operation room. Oxidized cellulose, due to its bioresorable, bactericidal and hemostatic properties, has long been used as a topical hemostatic wound dressing in a variety of surgical procedures, including neurosurgery, abdominal surgery, cardiovascular surgery, thoracic surgery, head and neck surgery, pelvic surgery, and skin and subcutaneous tissue procedures. Examples of hemostatic oxidized regenerated cellulose absorbable hemostats commercially available include Surgicel® absorbable hemostat, a knitted fabric of oxidized regenerated cellulose (ORC), Surgicel Nu-Knit® absorbable hemostat, a dense ORC fabric and Surgicel® Fibrillar absorbable hemostat, mircrofibrils of ORC, all available from Johnson & Johnson Wound Management Worldwide, a division of Ethicon, Inc., Somerville, N.J., a Johnson & Johnson Company.

Although the absorbency of body fluid and the hemostatic action of currently available oxidized cellulose hemostats are adequate for applications where mild to moderate bleeding is encountered, they are not known to be effective to prevent or stop severe bleeding where a relatively high volume of blood is lost at a relatively high rate. In such instances, e.g. arterial puncture, liver resection, blunt liver trauma, blunt spleen trauma, aortic aneurysm, bleeding from patients with over-anticoagulation, or patients with coagulopathies, such as hemophilia, etc., a higher degree of hemostasis is required quickly.

In an effort to achieve enhanced hemostatic properties additional chemical moieties, such as calcium, or biologics, such as fibrinogen, thrombin and fibrin, have been bound to oxidized cellulose fabrics. These biologics-bound combination products require the use of proteins derived from human or animal blood or tissue. This imposes a risk of blood-borne pathogen or zoonotic disease transmission by the products. Hemostatic wound dressings containing hemostatic agents are known. Woven or nonwoven fibrous materials are prepared by coating the materials with solutions containing ammonium salts of cellulose derivatives, e.g. free acid cellulose glycolic acid ether and free acid hydroxyproprionic acid ether. The coated material then is dried and preferably heated at elevated temperatures, e.g. 175-350° C., to obtain surgical dressings having insoluble hemostatic agent impregnant.

Medical sealants and adhesives, such as cyanoacrylate-based medical adhesives, function as hemostats only in very slowly diffusing bleeding. Sealant systems, usually involving chemical cross-linking steps, are not effective hemostatic agents on actively oozing or severely bleeding wound sites. The mobility of liquid sealants also makes it hard to apply manual or digital compression to help achieve hemostasis.

Currently available oxidized cellulose hemostats noted above are knitted fabrics having a porous structure. They exhibit good tensile and compressive strength and are flexible such that a physician can effectively place the hemostat in position and maneuver same during the particular procedure being performed.

While the various noted hemostatic materials and agents are known for use with respect to providing hemostasis for low to normal bleeding, to date none of the noted hemostats, or combinations thereof, have been shown to be effective in providing hemostasis in cases of severe bleeding, e.g. high volume and high rate of bleeding. The present invention provides such a hemostat that provides hemostasis in cases of severe bleeding.

SUMMARY OF THE INVENTION

The present invention is directed to wound dressings comprising a fabric having a wound-contacting surface and a top surface opposing the wound-contacting surface, the fabric comprising biocompatible fibers and having flexibility, strength and porosity effective for use as a hemostat; and a porous, polymeric matrix applied at least to the wound-contacting surface of the fabric and dispersed at least partially through said fabric in an amount effective to provide and maintain hemostasis for severe bleeding, wherein the polymeric matrix comprises a biocompatible, water-soluble or water-swellable polymer; and methods of making such wound dressings and fabrics.

DETAILED DESCRIPTION OF THE INVENTION

The present invention is directed to hemostatic fabrics and wound dressings fabricated at least in part from such fabrics, each of which provides and maintains effective hemostasis in cases of severe bleeding, where a relatively high volume of blood is lost at a relatively high rate. Examples of severe bleeding include, without limitation, arterial puncture, liver resection, blunt liver trauma, blunt spleen trauma, aortic aneurysm, bleeding from patients with over-anticoagulation, or bleeding from patients with coagulopathies, such as hemophilia. The present invention allows a patient to ambulate quicker than the current standard of care following, e.g. a diagnostic or interventional endovascular procedure.

Wound dressings of the present invention comprise a fabric having a wound-contacting surface and a top surface opposing the wound-contacting surface. The fabric comprises fibers and possesses physical properties suitable for use as a hemostat. Such properties include flexibility, strength and porosity. Dispersed at least on the wound contacting surface, and preferable through the fabric, is a porous polymeric matrix comprising a biocompatible, water-soluble or water-swellable polymer, in amounts effective to provide and maintain hemostasis in cases of severe bleeding.

The fabrics utilized in the present invention may be woven or nonwoven, provided that the fabric possesses the physical properties necessary for hemostasis. A preferred woven fabric has dense and knitted structure that provides form and shape for the hemostat.

The fibers comprise a biocompatible polymer. The fibers may be fabricated from any biocompatible polymer known for use in medical wound dressings. Such polymers include, without limitation, collagen, calcium alginate, chitin, polyester, polypropylene and cellulose. Preferred fibers comprise oxidized regenerated cellulose.

In preferred embodiments of the present invention, the absorbable hemostatic fabrics comprising the porous polymeric matrix dispersed there through are warp knitted tricot fabrics constructed of bright rayon yarn which is subsequently oxidized by known techniques. The fabrics are characterized by having a single ply thickness of at least about 0.5 mm, a density of at least about 0.03 g/cm$^2$, air porosity of less than about 150 cm$^3$/sec/cm$^2$ and liquid absorption capacity of at least about 3 times the dry weight of the fabric and at least about 0.1 g water per cm$^2$ of the fabric.

The knitted fabrics have good bulk without undue weight, are soft and drapable, conforming well to the configuration of the surface to which they are applied. The fabric may be cut into suitable sizes without running or fraying along the cut edge. Fabric strength after oxidation is more than adequate for use as a surgical hemostat.

Preferred hemostatic fabrics used in the present invention comprise oxidized cellulose and are best characterized by their physical properties of thickness, bulk, porosity and liquid absorption capacity as recited above. Suitable fabrics having these properties may be constructed by knitting 60 denier, 18-filament bright rayon yarn on a 32-gauge machine at a knit quality of 12. A suitable tricot fabric construction is front-bar 1-0, 10-11; back-bar 2-3, 1-0. The extended shog movement imparted to the front bar results in a 188 inch runner compared to a 70 inch runner for the back guide bar and increases the fabric bulk and density. The ratio of front to back bar runners in this particular construction is 1:2.68.

Typical physical and hemostatic properties of preferred fabrics produced as described above are noted in Table 1.

TABLE I

| Property | |
|---|---|
| Thickness (mm); | 0.645 |
| Density (g/cm$^2$); | 0.052 |
| Air Porosity (cm$^3$/sec/cm$^2$); | 62.8 |
| Tensile Strength[1](md/cd) Kg; | 1.9/4.5 |
| Elongation[2](%); | 23/49 |
| Absorption[3] | |
| (g/g fabric); | 3.88 |
| (g/cm$^2$ fabric); | 0.20 |
| Hemostasis[4] (min) | |
| 1 ply; | 5.7 ± 1.0 |
| 2 ply; | 5.6 ± 1.8 |

[1]tensile strength determined at 2 in/min extension md/cd = machine direction/cross direction.
[2]Elongation, machine direction/cross direction.
[3]Absorption based on weight of water absorbed by fabric.
[4]Hemostasis evaluation on incised porcine splenic wounds, time to stop bleeding.

The tricot fabrics utilized in the present invention may be constructed from bright rayon yarns of from about 40 to 80 total denier. Each yarn may contain from 10 to 25 individual filaments, although each individual filament is preferably less than 5 denier to avoid extended absorption times. The high bulk and fabric density are obtained by knitting at 28 gauge or finer, preferably at 32 gauge, with a fabric quality of about 10 or 12 (40 to 48 courses per inch). A long guide bar shog movement of at least 6 needle spaces, and preferably 8 to 12 spaces, further increases fabric thickness and density.

Other warp knit tricot fabric constructions which produce equivalent physical properties may, of course, be utilized in the manufacture of the improved hemostatic fabrics and wound dressings of the present invention, and such constructions will be apparent to those skilled in the art.

The polymer used to prepare fabrics and wound dressings of the present invention is a biocompatible, water-soluble or water-swellable polymer. The water-soluble or water-swellable polymer rapidly absorbs blood or other body fluids and forms a tacky or sticky gel adhered to tissue when placed in contact therewith. The fluid-absorbing polymer, when in a dry or concentrated state, interacts with body fluid through a hydration process. Once applied in a bleeding site, the polymer interacts with the water component in the blood via the hydration process. The hydration force provides an adhesive interaction that aids the hemostat adhere to the bleeding site. The adhesion creates a sealing layer between the hemostat and the bleeding site to stop the blood flow.

Polymers useful in preparing fabrics and wound dressings of the present invention include, without limitation, polysaccharides, polymethacrylic acids, polyamines, polyimines, polyamides, polyesters, polyethers, polynucleotides, polynucleic acids, polypeptides, proteins, poly (alkylene oxide), polythioesters, polythioethers, polyvinyls and mixtures thereof.

Polymers in preferred embodiments of the present invention comprise a water-soluble or water-swellable polysaccharide, preferably selected from the group consisting of methylcellulose, hydroxyalkyl cellulose, cellulose sulfate, water-soluble chitosan, salts of carboxymethyl cellulose, carboxymethyl cellulose (CMC), carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, heparin, heparin sulfate, heparan, heparan sulfate, dermatan sulfate, keratan sulfate, carrageenans, chitosan, starch, amylose, amylopectin and polyuronic acids including polymannuronic acid, polyglucuronic acid and polyguluronic acid. Most preferred is sodium carboxymethyl cellulose.

The composite hemostat of the present invention remains very flexible, conforms to a bleeding site, and retains good tensile and compressive strength to withstand handling during application. The hemostat can be cut into different sizes and shapes to fit the surgical needs. It can be rolled up or packed into irregular anatomic areas. The fabric in a preferred embodiment is a knitted oxidized regenerated cellulose (ORC), such as Surgicel Nu-Knit®, available from Ethicon, Inc., Somerville, N.J.

As noted above, the wound dressing of the present invention must comprise a porous polymeric matrix dispersed at least partially there through in order to provide and maintain hemostasis in cases of severe bleeding. A preferred method of making the porous polymeric matrix is to contact the fabric with the appropriate amount of polymer solution, thereby dispersing the dissolved polymer through the fabric, flash-freeze the polymer and fabric, and then remove the solvent from the frozen structure under vacuum, i.e. lyophilization. Through this preferred lyophilization method, a fabric comprising a matrix of the water-soluble or water-swellable polymer and having microporous or nanoporous structure is obtained. The lyophilization condition is important to the novel porous structure in order to create a large surface area in the hemostat with which body fluids can interact.

The features of such microporous structure can be controlled to suit a desired application by choosing the conditions to form the composite hemostat during lyophilization. To maximize the surface area of the porous matrix of the present invention, a preferred method is to quickly freeze the fabric/polymer construct at lower than 0° C., preferably at about −50° C., and to remove the solvent under high vacuum. The porous matrix produced thereby provides a large fluid absorbing capacity to the hemostatic wound dressing. When the hemostatic wound dressing comes into contact with body fluid, a very large surface area of polymer is exposed to the fluid instantly. The hydration force of the hemostat and subsequent formation of a tacky gelatinous layer helps to create an adhesive interaction between the hemostat and the bleeding site. The microporous structure of the polymeric matrix also allows blood to quickly pass through the fabric surface before the hydration takes place. The formation of a gelatinous sheet on oxidized cellulose upon blood contact will enhance the sealing property of the water-soluble gelatinous layer, which is critical to fast hemostasis for moderate to severe bleeding.

The fabric comprises polymer in an amount effective to provide and maintain hemostasis in cases of severe bleeding. If the ratio of polymer to fabric is too low, the polymer does not provide an effective seal to physically block the bleeding. If the ratio is too high, the composite hemostat wound dressing will be too stiff or too brittle to conform to wound tissue in surgical applications. Such an excessive ratio will also prevent the blood from quickly passing through the fabric surface to form the gelatinous layer on oxidized cellulose that is critical for enhancing the sealing property. A preferred weight ratio of polymer to fabric is from about 1:99 to about 15:85. A more preferred weight ratio of polymer to fabric is from about 3:97 to about 10:90.

In certain embodiments of the present invention, the porous polymeric matrix is dispersed substantially homogeneously on at least the wound-contacting surface of the fabric and through the fabric. In such cases, the fabric may be immersed in the polymer solution to provide homogeneous distribution throughout the fabric prior to lyophilization. In other embodiments, it is preferred that only the wound-contact surface of the hemostat sticks well to wet surfaces, while the physician handling side, or top surface of the fabric, does not. In such cases, the fabric may be partially immersed in the polymer solution so as to provide polymer at least on the wound-contact surface of the fabric. In this way, a gradient of polymer in the fabric is provided, whereby the fabric will comprise an effective amount of the lyophilized polymer adjacent the wound-contacting area, while the top surface of the fabric comprises little or no dispersed polymer and maintains ease of handling for the physician.

The present invention is best exemplified in the figures prepared by scanning electron microscope. The samples were prepared by cutting 1 $cm^2$ sections by using a razor. Micrographs of both top surface and wound-contacting surfaces and cross-sections were prepared and mounted on carbon stubs using carbon paint. The samples were gold-sputtered and examined by scanning electron microscopy (SEM) under high vacuum at 4 KV.

Figure 1:
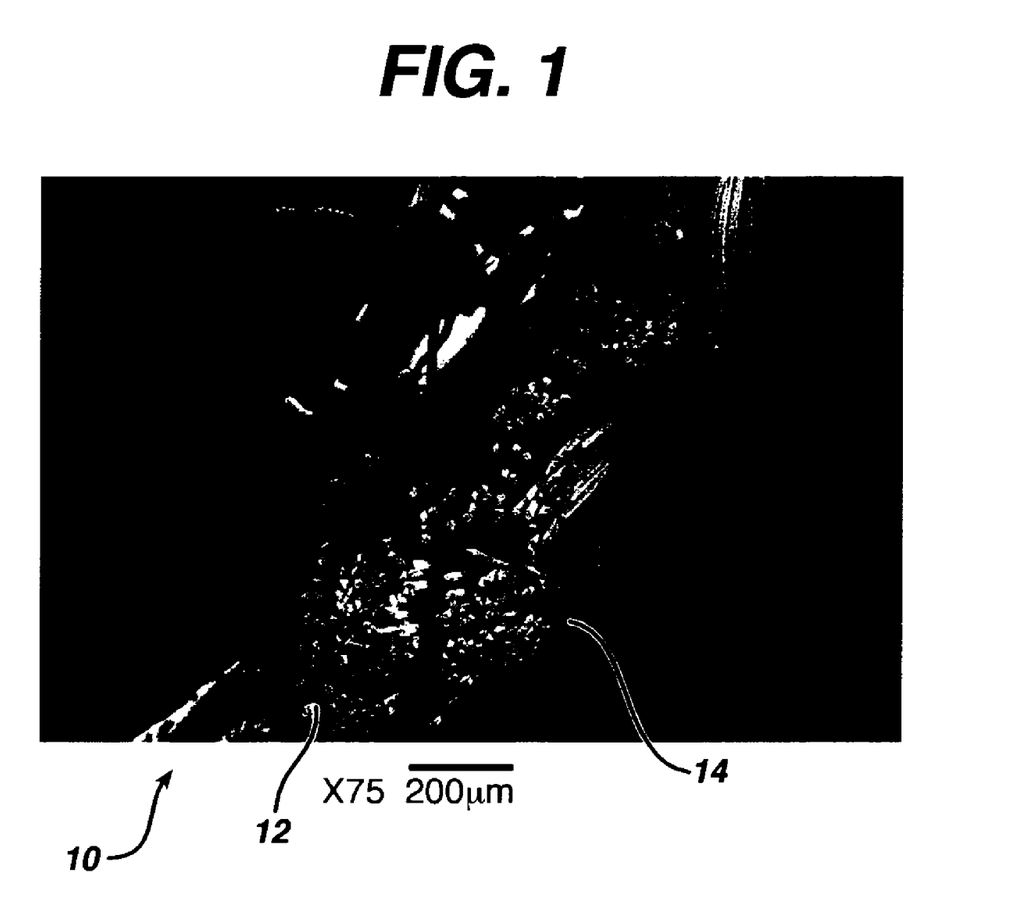
FIG. 1 is an image produced by scanning electron microscopy (×75) of a cross section of a comparative wound dressing.

FIG. 1 is a cross-section view (75×) of uncoated ORC fibers 12 organized as fiber bundles 14 and knitted into fabric 10 according to preferred embodiments of the invention discussed herein above. One commercial example of such a fabric is Surgicel Nu-Knit® absorbable hemostatic wound dressing.

Figure 2:
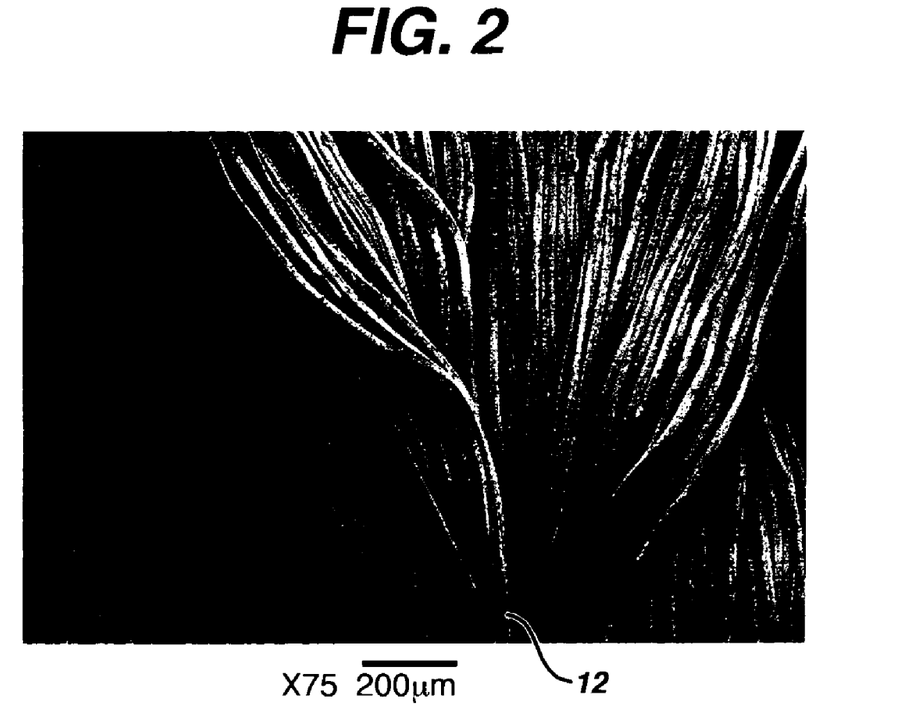
FIG. 2 is an image produced by scanning electron microscopy (×75) of the wound-contact surface of a comparative wound dressing.

FIG. 2 is a view of the wound-contact surface of the fabric of FIG. 1. Individual fibers 12 are shown within a bundle.

Figure 3:
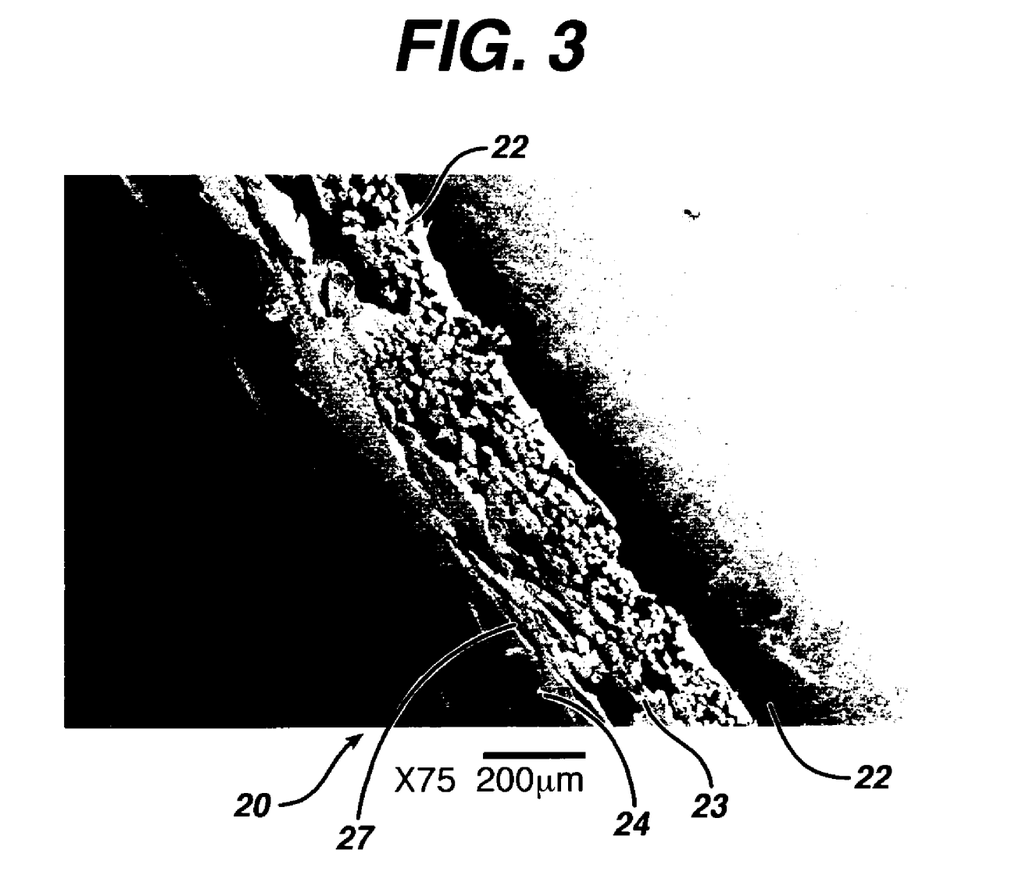
FIG. 3 is an image produced by scanning electron microscopy (×75) of a cross section of a comparative wound dressing.

FIG. 3 is a cross-section view of fabric 20 having wound-contact surface 22 and top surface 24 and that has been coated with a solution of sodium carboxymethyl cellulose (Na-CMC) and then air dried as in Example 6. Individual fibers 23 also are shown.

Figure 4:
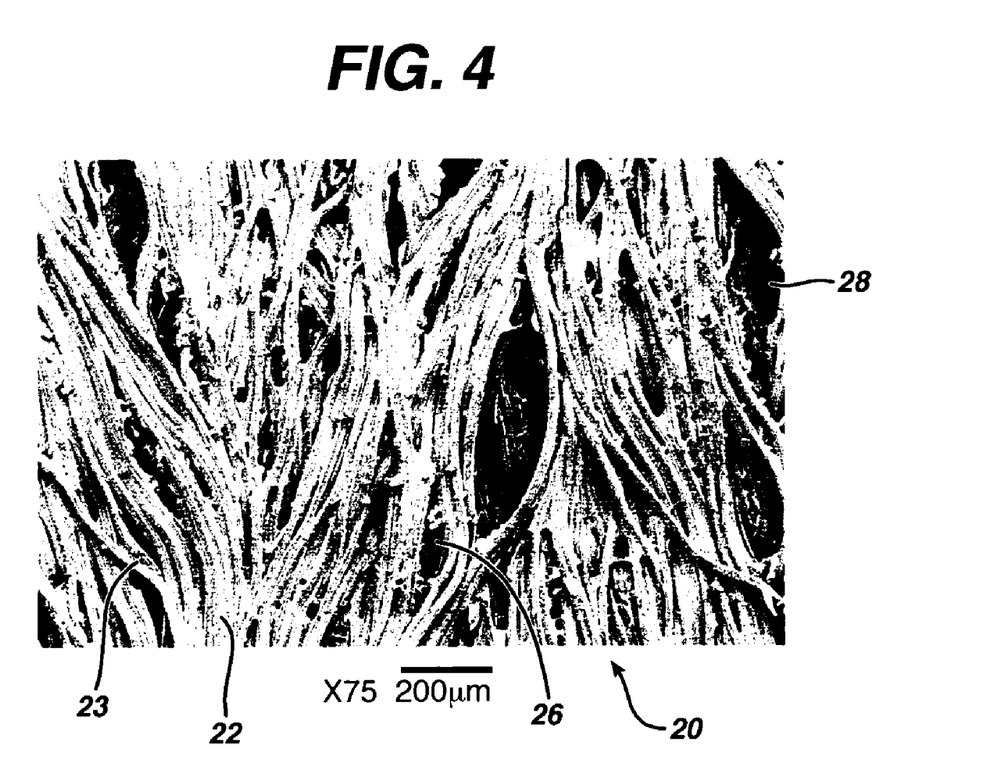
FIG. 4 is an image produced by scanning electron microscopy (×75) of the wound-contact surface of a comparative wound dressing.

FIG. 4 is a view of wound-contact surface 22 of fabric 20. As observed therein, in the course of air drying, polymer 26 agglomerates and adheres to fibers 23, in many instances adhering fibers 23 one to the other and creating large voids 28 in the hemostatic fabric through which body fluids may pass. Polymer 26 dispersed on and through fabric 20 is not in the state of a porous matrix and thus provides no hemostasis in cases of severe bleeding as described herein above due, at least in part, to a lack of sufficient porosity, e.g. surface area, to provide polymer/body fluid interaction effective to provide and maintain hemostasis in cases of severe bleeding.

Figure 5:
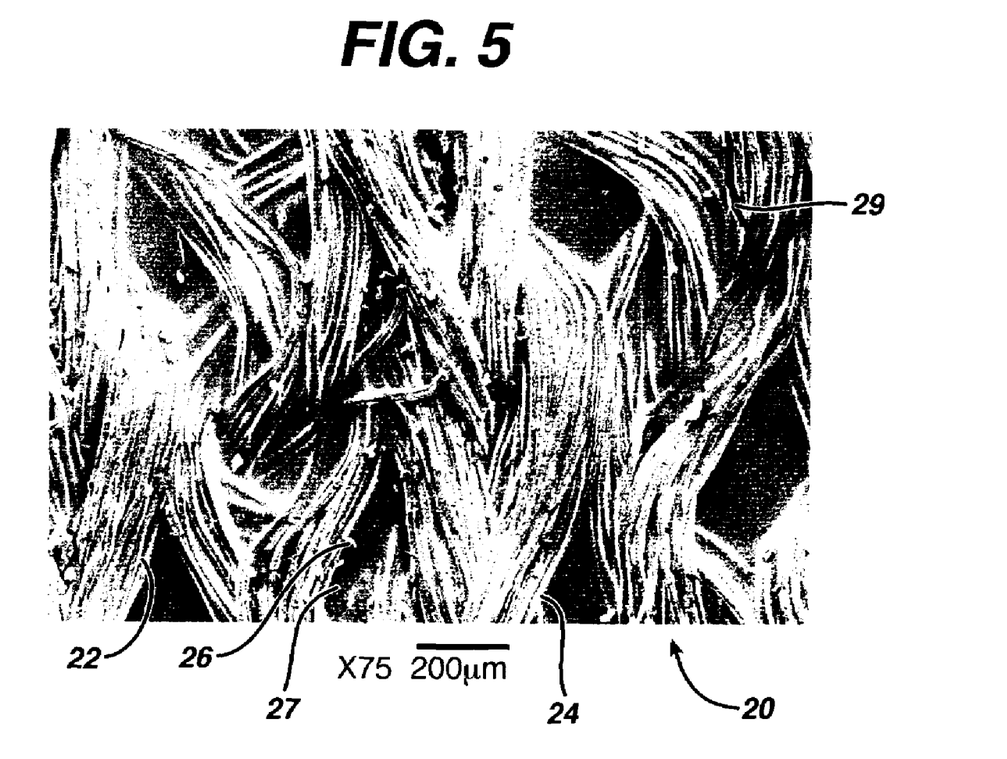
FIG. 5 is an image produced by scanning electron microscopy (×75) of the top surface of a comparative wound dressing.

FIG. 5 is a view of top surface 24 of fabric 20. As shown, top surface 24 contains a larger concentration of Na-CMC coating material as opposed to the wound-contact surface shown in FIG. 4, obscuring most of fibers 23, although the knitting pattern could still be discerned. The coating was thick enough to span across all of the fibers and generate an intact layer 27 of its own, also shown in FIG. 3. This layer appeared to be brittle, as cracks 29 in the coating were observed. The coating layer thickness varied from as thin as about 3 microns in some sections to about 30-65 microns in other sections.

In comparing the surface morphologies of wound-contact surface 22 and top surface 24 of fabric 20, it is apparent that wound-contact surface 22 contained significantly less Na-CMC. The coating was significantly thinner on the fibers than the coating on the top surface. While some Na-CMC was observed to span across some fibers, the coating was incomplete or had perforations present. The coating layer thickness, where present, did not exceed about 2 microns.

It is clear from FIGS. 3-5 that the fabrics prepared by air-drying do not contain a porous, polymeric matrix dispersed at least on the wound-contact surface and dispersed at least partially there through. As such, those fabrics do not provide and maintain hemostasis in cases of severe bleeding, as shown herein. In addition, such fabrics are brittle, stiff, do not conform to wound sites, are not handlable by physicians and generally are not suitable for use as wound dressings in cases of severe bleeding.

Figure 6:
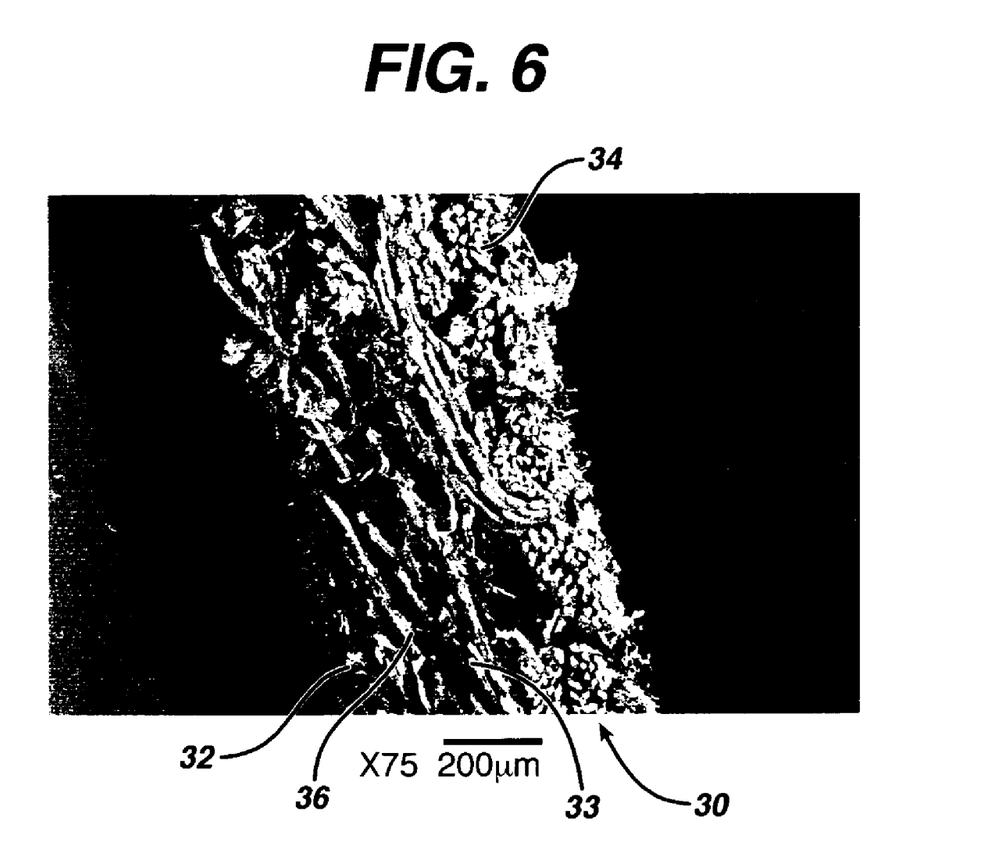
FIG. 6 is an image produced by scanning electron microscopy (×75) of a cross-section of a wound dressing of the present invention.
Figure 7:
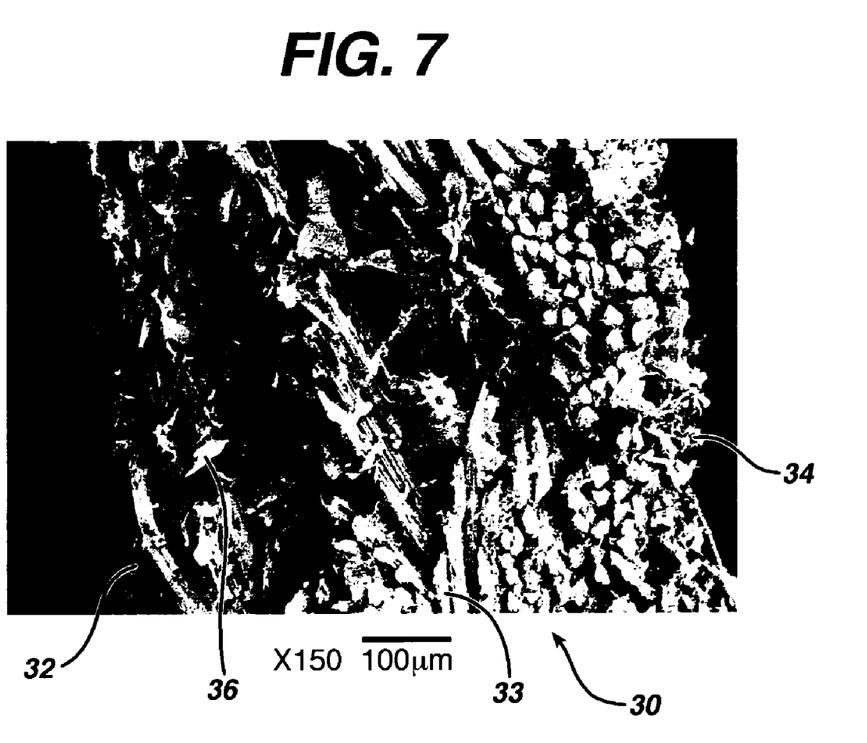
FIG. 7 is an image produced by scanning electron microscopy (×150) of a cross-section of a wound dressing of the present invention.

Hemostatic fabrics according to the present invention are set forth in FIGS. 6-9. As shown in FIGS. 6 and 7, a porous polymer matrix is more uniformly distributed on wound-contact surface 32 and throughout fabric 30. Polymer 36 forms a porous matrix integrated with the knitted fibers 33. The porous polymer matrix exhibits significant liquid absorption properties from capillary action in the same manner as a sponge.

Figure 8:
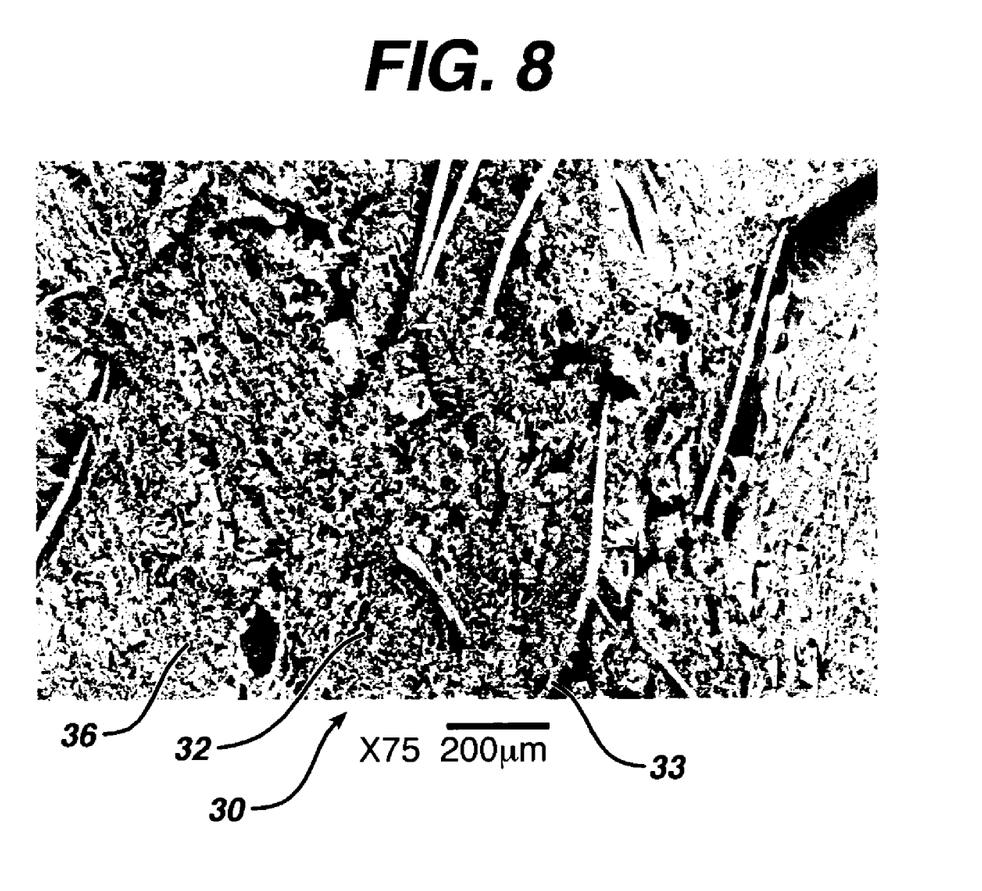
FIG. 8 is an image produced by scanning electron microscopy (×75) of the wound-contact surface of a wound dressing of the present invention.
Figure 9:
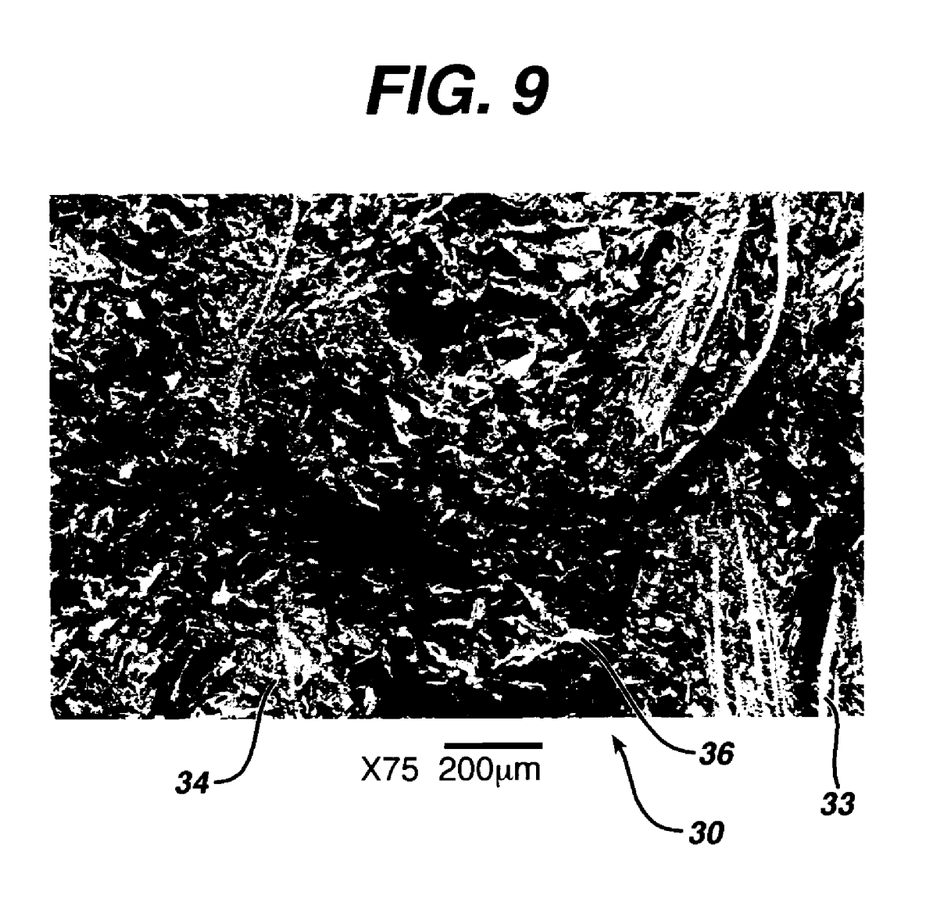
FIG. 9 is an image produced by scanning electron microscopy (×75) of the top surface of a wound dressing of the present invention.

As shown in FIGS. 8 and 9, the matrix disposed on the relative surfaces contains countless pores, ranging from about two microns to as large as about 35 microns in diameter or greater. FIG. 8 shows wound-contact surface 32 of fabric 30. As noted, polymer 36 is present in the form of a porous matrix about fibers 33, thereby providing ample polymer surface area with which body fluids can interact upon contact therewith. Top surface 34 shown in FIG. 9 also contains polymer 36 in the form of a porous matrix about fibers 33.

It is clear from FIGS. 6-9 that fabrics and wound dressings of the present invention contain a porous polymeric matrix dispersed on the wound-contact surface and substantially homogeneously through the fabric. Due to the porous nature of the matrix, body fluids are permitted to pass into the matrix, where ample surface area of polymer is present to interact with the body fluids. This results in faster and a higher degree of hemostasis, particularly where bleeding is occurring at a high volume/rate.

It also is clear from FIGS. 3-5 that comparative fabrics and wound dressings do not contain a porous polymeric matrix, either on a surface of the dressing or dispersed throughout the fabric. As a result, the amount of polymer present to interact with body fluids is significantly reduced. In addition, due to the formation of agglomerated polymer layers during air drying, body fluids are not permitted to pass freely into the wound dressing where they can interact with and bind to the dressing. Both of these characteristics results in less hemostasis, such that wound dressings of this construct do not provide and maintain hemostasis in cases of severe bleeding. Additionally, such fabrics were found to be brittle and stiff, such that placement within and conformance to a wound site by a physician is not acceptable.

In certain embodiments of the invention, a drug or a combination of pharmaceutical agents can be incorporated into the hemostat. To fabricate such a hemostat, a drug or agent is first dissolved with a polymer in a solvent. The fabric is then coated with the polymer/drug solution, and the solvent is removed through lyophilization. Preferred drugs and agent include analgesics, anti-infective agents, antibiotics, adhesion preventive agents, procoagulants and wound healing growth factors.

While the following examples demonstrate certain embodiments of the invention, they are not to be interpreted as limiting the scope of the invention, but rather as contributing to a complete description of the invention.

EXAMPLE 1

ORC/HEC Porous Patch Preparation:

One gram of hydroxyethyl cellulose (HEC, from Aldrich) was dissolved in 99 grams of deionized water. After complete dissolution of the polymer, 10 grams of the HEC solution was transferred into a crystallization dish with a diameter of 10 cm. A piece of Surgicel Nu-Knit® absorbable hemostat, based on oxidized regenerated cellulose (ORC), having a diameter of 9.8 cm (about 1.3 gram) was placed on the HEC solution in the crystallization dish. After soaking the fabric in the solution for 3 minutes, the wet fabric in the dish was then lyophilized overnight. A very flexible patch was formed. The patch was further dried at room temperature under vacuum.

EXAMPLE 2

ORC/CS Porous Patch Preparation

One gram of cellulose sulfate (CS, from ACROS Organics) was dissolved in 99 grams of deionized water. After complete dissolution of the polymer, 10 grams of the CS solution was transferred into a crystallization dish with a diameter of 10 cm. A piece of Surgicel Nu-Knit® fabric with a diameter of 9.8 cm (about 1.3 gram) was placed on the CS solution in the crystallization dish. After soaking the fabric for 3 minutes, the wet fabric was then lyophilized overnight. A very flexible patch was formed. The patch was further dried at room temperature under vacuum.

EXAMPLE 3

ORC/MC Porous Patch Preparation

One gram of methyl cellulose (MC, from Aldrich) was dissolved in 99 grams of deionized water. After complete dissolution of the polymer, 10 grams of the MC solution was transferred into a crystallization dish with a diameter of 10 cm. A piece of Surgicel Nu-Knit® fabric with a diameter of 9.8 cm (about 1.3 gram) was placed on the MC solution in the crystallization dish. After soaking the fabric for 3 minutes, the wet fabric in the dish was then lyophilized overnight. A very flexible patch was formed. The patch was further dried at room temperature under vacuum.

EXAMPLE 4

ORC/Water-Soluble Chitosan (WS-CH) Porous Patch Preparation

One gram of WS-CH was dissolved in 99 grams of deionized water. After complete dissolution of the polymer, 10 grams of the WS-CH solution was transferred into a crystallization dish with a diameter of 10 cm. A piece of Surgicel Nu-Knit® fabric with a diameter of 9.8 cm (about 1.3 gram) was placed on WS-CH solution in the crystallization dish. After soaking the fabric for 3 minutes, the wet fabric in the dish was then lyophilized overnight. A very flexible patch was formed. The patch was further dried at room temperature under vacuum.

EXAMPLE 5

ORC/Na-CMC Porous Patch Preparation

One gram of sodium salt of CMC (Na-CMC, from Aqualon) was dissolved in 99 grams of deionized water. After complete dissolution of the polymer, 10 grams of the Na-CMC solution was transferred into a crystallization dish with a diameter of 10 cm. A piece of Surgicel Nu-Knit® fabric with a diameter of 9.8 cm (about 1.3 gram) was placed on the CMC solution in the crystallization dish. After soaking the fabric for 3 minutes, the wet fabric in the dish was then lyophilized overnight. A very flexible patch was formed. The patch was further dried at room temperature under vacuum.

COMPARATIVE EXAMPLE 6

ORC/Na-CMC Film Preparation

One gram of sodium salt of CMC (Na-CMC, from Aqualon) was dissolved in 99 grams of deionized water. After complete dissolution of the polymer, 10 grams of the Na-CMC solution was transferred into a crystallization dish with a diameter of 10 cm. A piece of Surgicel Nu-Knit® fabric with a diameter of 9.8 cm (about 1.3 gram) was placed on the Na-CMC solution in the crystallization dish. The wet fabric in the dish was then air-dried overnight. A rigid and brittle patch was formed. The ORC/Na-CMC film was further dried at room temperature under vacuum. The film was not effective as a hemostat because it was too stiff and did not conform to the bleeding site well.

EXAMPLE 7

Na-CMC Porous Patch Preparation

One gram of sodium salt of CMC (Na-CMC, medium viscosity grade from Sigma) was dissolved in 99 grams of deionized water. After complete dissolution of the polymer, 60 grams of the Na-CMC solution was transferred into a crystallization dish with a diameter of 10 cm. The solution in the dish was then lyophilized overnight. A porous sponge was formed. The patch was further dried at room temperature under vacuum.

EXAMPLE 8

Hemostatic Performance of Different Materials in Porcine Splenic Incision Model

A porcine spleen incision model was used for hemostasis evaluation of different materials. The materials were cut into 2.5 cm×1.5 cm rectangles. A linear incision of 1.5 cm with a depth of 0.3 cm was made with a surgical blade on a porcine spleen. After application of the test article, digital tamponade was applied to the incision for 2 minutes. The hemostasis was then evaluated. Additional applications of digital tamponade for 30 seconds each time were used until complete hemostasis was achieved. Fabrics failing to provide hemostasis within 12 minutes were considered to be failures. Table 1 lists the results of the evaluation.

TABLE 1

Hemostatic performance of different materials

| Material | Percent of test samples to achieve hemostasis within the time period | | | | | |
| --- | --- | --- | --- | --- | --- | --- |
| | 0-2 (min) | 2-3 (min) | 3-4 (min) | 4-5 (min) | 5-6 (min) | <12 (min) |
| Surgicel Nu-Knit ® fabric | 0% | 0% | 100% | | | |
| Example 1 patch | 100% | | | | | |
| Example 2 patch | 100% | | | | | |
| Example 3 patch | 100% | | | | | |
| Example 4 patch | 100% | | | | | |
| Example 5 patch | 100% | | | | | |
| Example 6 film | | | 50% | | 50% | |
| Example 7 sponge | | | | | | 0 |
| Surgical gauze | | | | | | 0 |

As indicated from the results, wound dressings prepared using lyophilization as the means for removing solvent improved hemostatic property of hemostatic fabrics, while the air-dried process failed to enhance the hemostatic property of hemostatic fabrics. Additionally, lyophilized Na-CMC sponge alone failed to achieve hemostasis.

EXAMPLE 9

Hemostatic Performance of Example 5 (ORC/Na-CMC) in a Porcine Splenic Arterial Needle Puncture Model A puncture defect was made on a porcine splenic artery with an 18-gauge needle. After the needle was removed, severe bleeding was observed. A test article (2.5 cm×2.5 cm) was applied over the puncture site. Digital pressure was applied over the test article for 2 minutes. The hemostatic performance was evaluated. The observations are listed in Table 2.

TABLE 2

Comparison of Initial time to Hemostasis and Ability of Maintaining Hemostasis

| Material | # of Digital Pressure | Initial Time to Hemostasis | Maintenance of Hemostasis |
| --- | --- | --- | --- |
| Surgicel Nu-Knit ® | 1 | <2 min | Re-bleeding occurred after 4 min |
| Example 5 Patch | 1 | <2 min | No Re-bleeding occurred |

EXAMPLE 10

Hemostatic Performance of Different Materials in a Porcine Splenic Incision Model with Tamponade for 30 Seconds A porcine spleen incision model was used for hemostasis evaluation of different materials. The materials were cut into 2.5 cm×1.5 cm rectangles. A linear incision of 1.5 cm with a depth of 0.3 cm was made with a surgical blade on porcine spleen. After application of the test article, digital tamponade was applied to the incision for 30 seconds. The hemostasis evaluation was then performed. Additional applications of digital tamponade for 30 seconds each time were used until complete hemostasis was achieved. Table 3 lists the results of the evaluation.

TABLE 3

Hemostatic performance of different materials in a splenic incision model

| Material | # of Digital Pressure | Time to Hemostasis |
|---|---|---|
| Surgicel Nu-Knit ® | 5 | 2 min 55 sec |
| Example 5 Patch | 1 | <30 sec |

EXAMPLE 11

Hemostatic Performance of Different Materials in a Porcine Splenic Cross-Hatch Model A porcine spleen cross-hatch model was used for hemostasis evaluation of different materials. The materials were cut into 3 cm×3 cm squares. A surgical defect (2 cm×2 cm, 0.2 cm deep) was made with a surgical blade on the porcine spleen. Additional bleeding was induced by making three additional equally spaced, side-to-side horizontal incisions and three additional equally spaced, side-to-side vertical incisions within the defect. After application of the test article, digital tamponade was applied to the incision for 2 minutes. The hemostasis evaluation was then performed. Additional applications of digital pressure for 30 second each time were used until complete hemostasis was achieved. Table 4 lists the results of the evaluation.

TABLE 4

Hemostatic performance of different materials in a splenic cross-hatch model

| Material | # of Digital Pressure | Time to Hemostasis |
|---|---|---|
| Surgicel Nu-Knit ® | 4 | 3 min 55 sec |
| Example 5 Patch | 1 | <2 min |

We claim:

1. A process for making a wound dressing for use with moderate to severe bleeding, the wound dressing comprising a fabric that comprises oxidized regenerated cellulose fibers and a biocompatible, water-soluble or water-swellable polymer matrix of sodium carboxymethyl cellulose, the process consisting of the steps of:
   providing a solution having dissolved therein sodium carboxymethyl cellulose,
   providing a fabric having a top surface and a bottom surface opposing said top surface, said fabric having flexibility, strength and porosity effective for use as a hemostat,
   immersing said fabric at least partially in said solution to distribute said solution at least partially through said fibers,
   lyophilizing said fabric and said solution distributed at least partially through said fibers, thereby forming a porous polymeric matrix at least partially integrated with or about the fibers having a microporous structure with a large fluid absorbing capacity.

2. The process of claim 1 wherein said fabric is knitted.

3. The process of claim 1 wherein the weight ratio of said sodium carboxymethyl cellulose to said fabric is from about 1:99 to about 20:80.

4. The process of claim 3 wherein the weight ratio of said sodium carboxymethyl cellulose to said fabric is from about 3:97 to about 10:90.

5. A hemostatic wound dressing made in accordance with the process of claim 1.

6. The wound dressing of claim 5 wherein the fibers are woven or nonwoven.

7. The wound dressing of claim 5 wherein the fibers are knitted.

8. The wound dressing of claim 5 wherein the weight ratio of said sodium carboxymethyl cellulose to said fabric is from about 1:99 to about 20:80.

9. The wound dressing of claim 8 wherein the weight ratio of said sodium carboxymethyl cellulose to said fabric is from about 3:97 to about 10:90.

* * * * *